United States Patent [19]

Bringhurst et al.

[11] Patent Number: Plant 7,615

[45] Date of Patent: Aug. 6, 1991

[54] STRAWBERRY PLANT CALLED "CAPITOLA"

[75] Inventors: Royce S. Bringhurst, Davis; Victor Voth, Santa Ana, both of Calif.

[73] Assignee: The Regents of the University of California, Berkeley, Calif.

[21] Appl. No.: 479,315

[22] Filed: Feb. 13, 1990

[51] Int. Cl.[5] ..... A01H 5/08

[52] U.S. Cl. ..... Plt./49

[58] Field of Search ..... Plt./48, 49

*Primary Examiner*—James R. Feyrer

*Attorney, Agent, or Firm*—Townsend and Townsend

[57] ABSTRACT

'Capitola' is a new day-neutral type of strawberry variety with perhaps the highest potentiality for yield of any cultivar yet released. It is also noteworthy for large fruit size, symmetry, attractive appearance and general flexiblity in planting requirements.

2 Drawing Sheets

DESCRIPTION

This invention relates to a new and distinctive day-neutral type strawberry cultivar designated as 'Capitola' which is the result of a cross between CA 75.121-101×Parker (U.S. Plant Pat. No. 5,263), made in 1983.

'Capitola' first fruited at the University of California Wolfskill Experimental Orchards near Davis, Calif. in 1984, where it was selected and designated originally as CA 83.93-6. It was tested later as advanced selection CN 93.

'Capitola' has been propagated asexually by runners and has been tested at various University of California field stations and research facilities and to a very limited extent in growers' fields under Test Agreement.

In the photographs:

Figure 1:
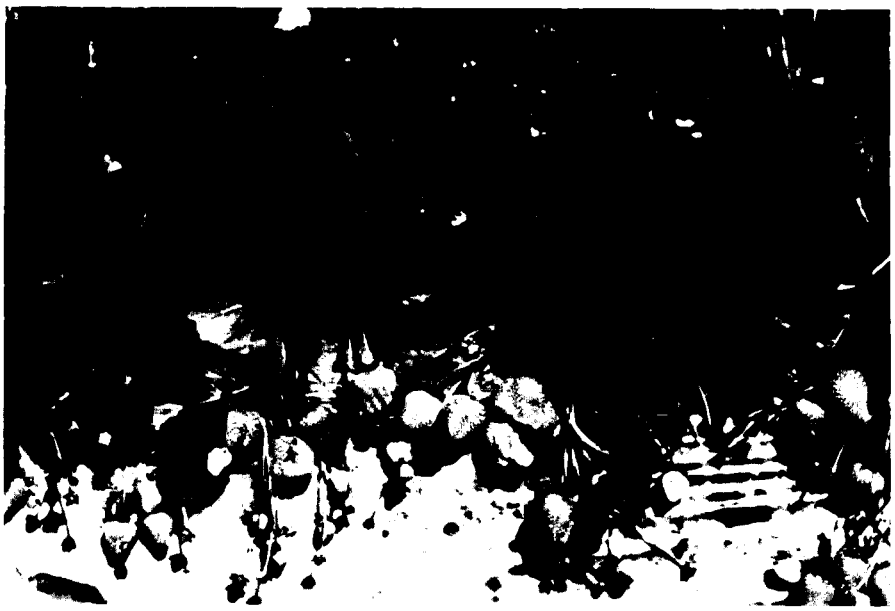
FIG. 1 shows typical growth, flowering and fruiting characteristics of the plant.
Figure 2:
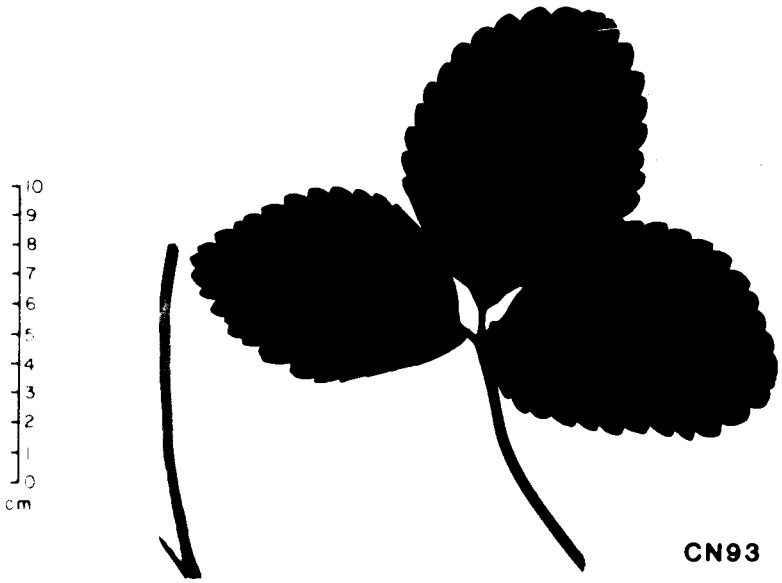
FIG. 2 shows a typical midsummer mature leaf from a plant in full fruit.
Figure 3:
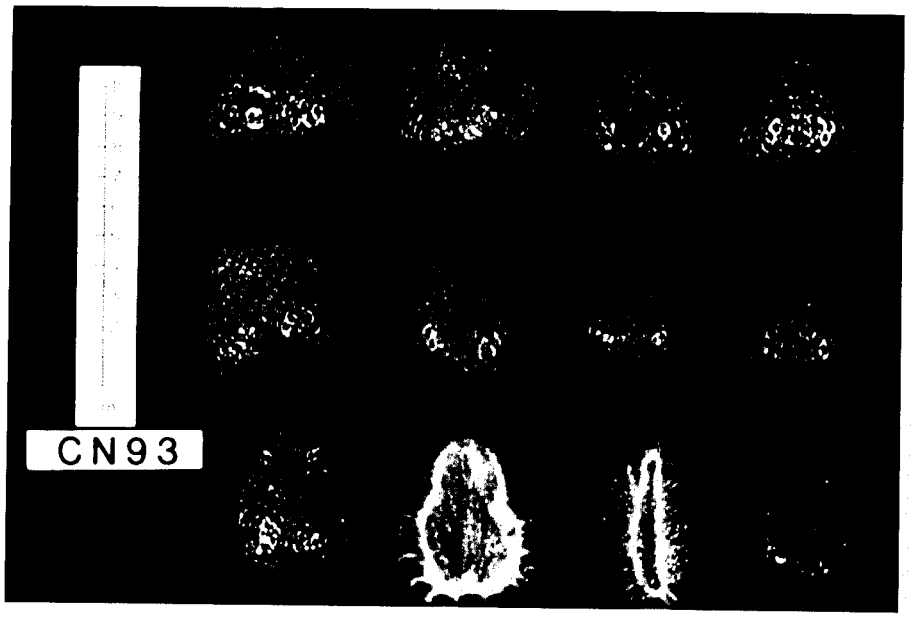
FIG. 3 shows representative early-season fruit with longitudinal and cross-sectional views.

'Capitola' commences fruiting about three months after planting, whether fresh dug or cold storage plants are used, regardless of planting time provided that satisfactory growing conditions prevail. 'Capitola' is a stronger day-neutral than 'Selva' (U.S. Plant Pat. No. 5,266), or 'Muir' (U.S. Plant Pat. No. 6,558), but not quite as strong as 'Hecker' (U.S. Plant Pat. No. 4,507) or 'Fern' (U.S. Plant Pat. No. 3,267). The difference is most evident in the nursery where the mother and most of the daughter plants tend to flower and fruit whereas only the daughter plants of 'Selva' tend to flower and fruit. 'Capitola' is heterozygous for the day-neutral trait.

Plants and foliage

Fruiting 'Capitola' plants are larger and somewhat more erect in growth flowering habit than those of 'Selva' but less erect in flowering habit than 'Muir' or 'Irvine'. Foliar characteristics from mid-summer 1988 central coast grown fruiting plants of 'Capitola' are compared with those of 'Irvine', 'Muir', 'Selva', and 'Fern' in Table 1.

TABLE 1

| | CAPITOLA | IRVINE | MUIR | SELVA | FERN |
|---|---|---|---|---|---|
| Munsell Color | 7.5GY4/4 | 7.5GY4/4 | 2.5GY4/3 | 7.5GY4/4 | 7.5GY4/4 |
| Shape (length/width) | 1.17 | 1.10 | 1.02 | 1.10 | 1.14 |
| Base angle of terminal leaflet | 55° | 53° | 60° | 55° | 50° |
| Size of terminal leaflets | 90 | 76 | 84 | 81 | 76 |
| Serrations of terminal leaflets | 11.2 | 9.4 | 11.2 | 11.2 | 12.0 |
| Petiolule length (MM) | 6.6 | 6.6 | 6.6 | 10.4 | 6.4 |
| Petiole length (MM) | 209 | 150 | 137 | 152 | 154 |

As shown above 'Capitola' leaves are about the same color as those of 'Selva', 'Fern' and 'Irvine' but lighter and more yellow than those of 'Muir' (Munsell Color System—Nickerson Color Fan). Terminal leaflets are only slightly longer in relation to width than those of 'Selva', 'Fern' or 'Irvine' but less round than those of 'Muir' as shown by the length/width measurement and half-blade terminal leaflet basal angle. 'Capitola' terminal leaflets are somewhat larger than those of the comparison cultivars as determined by extracting the square root of the length×width measurements. Terminal leaflet serration numbers are about the same as those for all the comparison cultivars except 'Irvine' which has less. The length of the terminal leaflet petiolules of 'Capitola' is about the same as those of all the comparison cultivars except 'Selva' which has longer ones. 'Capitola' plants are considerably larger than those of any of the comparision cultivars as indicated by petiole length. Similar to 'Irvine', bract leaflets are rare on 'Capitola'. Runner production in nursery plants of 'Capitola' is quite good, about equal or better than for 'Selva' and 'Muir'.

Isozymes in leaf extracts

'Capitola' has been classified for three enzyme systems by starch gel electrophoresis: A. Phosphoglucoisomerase (PGI); B. Leucine Amino Peptidase (LAP); and C. Phosphoglucomutase (PGM); and the results are compared with those for other day-neutral California cultivars in Table 2.

TABLE 2

| | CAPITOLA & MRAK | IRVINE | MUIR |
|---|---|---|---|
| PGI | A1 | A3 | A2 |
| LAP | B3 | B1 | B1 |
| PGM | C2 | C1 | C2 |

| | SELVA | HECKER | APTOS & BRIGHTON | YOLO |
|---|---|---|---|---|
| PGI | A2 | A1 | A4 | A1 |
| LAP | B3 | B1 | B3 | B1 |
| PGM | C2 | C4 | C4 | C2 |

Thus, 'Capitola' with the pattern A1, B3 and C2 can be distinguished from all other U. C. day-neutrals with these three systems except 'Mrak' to which it is identical. For the procedure: J. Amer. Soc. Hort. Sci. 106:684–687, 1981).

Disease and pest reaction

'Capitola' is highly resistant to (tolerant of) the virus diseases common in California including "Mild Yellow Edge" and complexes containing it and is quite susceptible to common leaf spot (Ramularia), and is moderately susceptible to the two-spotted mite.

Flowering, fruiting, fruit and production characteristics

'Capitola' is similar to California day-neutral cultivars 'Selva' and 'Muir' in that with a minimum of conditioning, it will flower and fruit anytime, effectively independent of day length. Flowers are borne on long, relatively thick peduncles, much less erect as those of 'Muir' or 'Irvine' but more erect than those of 'Selva'. The flowers have large petals averaging about six. 'Capitola' is self-fertile providing ample pollen throughout the season and pollination is generally good as relatively few malformed fruit form.

All of our measurements show that 'Capitola' is capable of yielding more than any of the other day-neutral and short-day type cultivars that we know of and with fruit size as large or larger on the average as that of 'Selva' (Tables 3, and 4). 'Capitola' may have as low or lower a chilling requirement than 'Selva' and it might be possible to plant it earlier than 'Selva' with favorable results.

'Capitola' fruit shape is characteristically symmetrically medium conic. The frluit of 'Capitola' is less firm than that of most of the other day-neutral cultivars as measured by a penetrometer equipped with a "Hunter Force Gauge" (Tables 4 and 5). 'Capitola' fruit quality characteristics (ascorbic acid, soluble solids, titratable acid and color) are compared with those of 'Chandler', 'Douglas', 'Irvine', 'Oso Grande', and 'Selva' from plants grown under optimum conditions under the "hill" system in winter plantings at the University of California Strawberry Research Facility, Watsonville, in Table 5. Table 3. Comparing the 1988 harvest of 'Capitola' over eight winter plantings and the 1989 harvest over four with those of appropriate cultivars at Watsonville. Means with the same letter not significantly different (5%).

| ITEM | TOT YLD G/PL | SIZE G/FR | FIRM PENET | AP SCORE | PERF* SCORE |
|---|---|---|---|---|---|
| 1988 Harvest | | | | | |

-continued

| ITEM | TOT YLD G/PL | SIZE G/FR | FIRM PENET | AP SCORE | PERF* SCORE |
|---|---|---|---|---|---|
| Capitola | 1758 a | 23.9 a | 6.3 cd | 3.5 a | 35.5 a |
| Fern | 1381 a | 20.2 c | 6.1 d | 3.1 cd | 31.4 bc |
| Irvine | 1309 bc | 21.6 b | 7.8 a | 3.2 c | 33.1 ab |
| Selva | 1305 bc | 22.3 b | 7.8 a | 3.3 b | 33.4 ab |
| Muir | 1090 cd | 21.6 b | 7.2 b | 3.1 cd | 29.9 cd |
| Mrak | 1081 cd | 17.6 d | 6.5 c | 3.0 d | 27.9 d |
| Yolo | 938 d | 19.3 c | 7.1 b | 3.0 d | 27.2 d |
| 1989 Harvest | | | | | |
| Capitola | 2725 a | 26.5 a | 4.4 e | 2.8 1 | 45.1 a |
| Oso Grande | 1788 bc | 26.9 a | 6.6 a | 3.1 b | 38.4 bc |
| Irvine | 1710 bc | 21.8 b | 6.5 abc | 2.9 cd | 35.4 cd |
| Selva | 1528 c | 22.6 b | 6.6 ab | 3.1 bc | 34.3 d |
| Muir | 1523 c | 22.1 b | 6.0 c | 2.9 d | 33.2 d |
| Chandler | 1491 c | 25.6 a | 5.3 d | 3.4 a | 34.2 d |

*Performance Score =

$$\frac{\text{TOTAL YLD}}{100} + \frac{\text{SIZE}}{3} + \text{FIRM} = 1.6\ (\text{AP SCORE})$$

TABLE 4

Comparing the 1987 harvest of 'Capitola' with that of 3 standard short-day type cultivars and 3 day-neutral cultivars in a summer planting made at Watsonville 3 Sept. 86.

| CULTIVAR | G/PL BY 6 WKS ENDING 5/6 | 617 | 7/29 | 9/16 | TOT YLD G/PL |
|---|---|---|---|---|---|
| Chandler | 436 | 917 | 576 | 297 | 2227 |
| Oso Grande | 500 | 638 | 241 | 177 | 1559 |
| Pajaro | 423 | 621 | 300 | 202 | 1548 |
| Capitola | 21 | 985 | 774 | 558 | 2339 |
| Muir | 359 | 596 | 332 | 232 | 1521 |
| Selva | 417 | 522 | 266 | 219 | 1425 |
| Yolo | 451 | 311 | 166 | 105 | 1034 |

| CULTIVAR | TOT YLD S.D. | SIZE G/FR | FIRM PENET | AP. SCORE | PERF.* SCORE |
|---|---|---|---|---|---|
| Chandler | 255 | 16.5 | 4.7 | 3.1 | 37 |
| Oso Grande | 49 | 20.5 | 6.3 | 2.9 | 32 |
| Pajaro | 85 | 19.8 | 5.2 | 3.1 | 32 |
| Capitola | 67 | 26.0 | 5.1 | 3.5 | 44 |
| Muir | 36 | 22.3 | 5.4 | 3.1 | 33 |
| Selva | 287 | 22.1 | 6.0 | 3.1 | 32 |
| Yolo | 17 | 19.2 | 4.9 | 3.5 | 26 |

*Performance Score -

$$\frac{\text{TOTAL YLD}}{100} + \frac{\text{SIZE}}{3} + \text{FIRM} = 1.6\ (\text{AP SCORE})$$

TABLE 5

Fruit quality measurements and color, Watsonville 8 May 1989. Means with same letter not significantly different (5%)

| CULTIVAR | ASCORBIC ACID mg/100 g | SOL SOLIDS % | TIT. ACID % | COLOR |
|---|---|---|---|---|
| Chandler | 51 a | 7.3 a | 0.69 b | 5R4/12 |
| Douglas | 43 bc | 6.8 b | 0.72 b | 6R4/12 |
| Irvine | 41 cd | 6.9 ab | 0.66 bc | 7R5/14 |
| Oso Grande | 40 cd | 5.7 c | 0.52 d | 7.5R4.5/11 |
| Capitola | 39 d | 6.7 b | 0.91 a | 5R4/12 |
| Selva | 33 e | 7.1 ab | 0.59 cd | 7R4/11 |

'Capitola' fruit averaged almost as high in ascorbic acid content as 'Douglas', 'Irvine', 'Irvine' and 'Oso Grande', less than 'Chandler', but more than 'Selva' as measured by the Loeffler and Ponting method (1942, J. Indust. and Engin. Chem. 14:846). 'Capitola' fruit was in the middle grouping on soluble solids but highest of all in titratable acids (ibid).

The fruit skin color is about the same as that of 'Chandler', 'Pajaro' or 'Douglas' (ibid). The flesh color is about the same as that of the skin. The achenes are bright yellow to slightly reddish, positioned about flush with the skin surface. The calyx is medium to large sized, positioned about even with the base of the fruit.

The flavor of 'Capitola' is pleasantly sub-acid as good or better than that of 'Selva' and is slightly more juicy. The fruit is recommended for fresh market and processing, for commercial planting and home gardening, particularly where "off season" fruiting is desirable. The only cultivars that 'Capitol' resembles closely in performance are 'Selva' and 'Muir' and consequently it is of interest wherever they are currently grown.

We claim:

1. The new and distinct variety of strawberry plant herein described and illustrated and identified by the characteristics enumerated above.

* * * * *